US00RE43732E

(19) United States
(12) Reissued Patent
Hedrick

(10) Patent Number: US RE43,732 E
(45) Date of Reissued Patent: Oct. 16, 2012

(54) PRESSURE-BASED AIRCRAFT FUEL CAPACITY MONITORING SYSTEM AND METHOD

(75) Inventor: Geoffrey S. M. Hedrick, Malvern, PA (US)

(73) Assignee: Innovative Solutions and Support, Inc., Exton, PA (US)

(21) Appl. No.: 13/044,498

(22) Filed: Mar. 9, 2011

Related U.S. Patent Documents

Reissue of:
(64) Patent No.: 7,669,473
Issued: Mar. 2, 2010
Appl. No.: 11/432,022
Filed: May 11, 2006

U.S. Applications:
(60) Provisional application No. 60/679,752, filed on May 11, 2005.

(51) Int. Cl.
*G01F 23/00* (2006.01)
(52) U.S. Cl. ..... 73/299
(58) Field of Classification Search ..... 73/299, 73/290 B, 438; 702/55, 156
See application file for complete search history.

(56) References Cited

U.S. PATENT DOCUMENTS

| | | | | |
|---|---|---|---|---|
| 3,590,843 | A * | 7/1971 | Meyer | 137/807 |
| 4,043,193 | A | 8/1977 | Bailey | 73/152.51 |
| 4,630,478 | A * | 12/1986 | Johnson | 73/299 |
| 4,669,309 | A * | 6/1987 | Cornelius | 73/299 |
| 4,711,127 | A * | 12/1987 | Hafner | 73/302 |
| 5,347,863 | A * | 9/1994 | Richard | 73/301 |
| 5,791,187 | A * | 8/1998 | Chang | 73/299 |
| 6,510,736 | B1 * | 1/2003 | Van Ee | 73/299 |
| 6,542,848 | B1 * | 4/2003 | Neeser et al. | 702/156 |
| 2002/0065627 | A1 * | 5/2002 | Neeser et al. | 702/156 |
| 2003/0110856 | A1 * | 6/2003 | Su | 73/299 |

FOREIGN PATENT DOCUMENTS

| | | |
|---|---|---|
| FR | A-2 623 105 | 5/1989 |
| GB | A-2 186 086 | 8/1987 |

(Continued)

*Primary Examiner* — Peter Macchiarolo
*Assistant Examiner* — Tamiko Bellamy
(74) *Attorney, Agent, or Firm* — Bryan Cave LLP

(57) ABSTRACT

Dynamic monitoring of the amount of fuel remaining in an aircraft fuel tank is effected by delivering a constant volume flow of an inert gas into the fuel through the respective open distal ends of a sensor conduit tube and a reference conduit tube, each of which extends from a proximal end exterior of the tank to its respective distal open end located within the fuel tank. The sensor conduit tube distal end is fixed closely proximate the bottom of the tank, and the reference conduit tube distal end is fixed proximate but at a vertical spacing h from the sensor conduit tube distal end. The pressure at which the gas is delivered into the fuel at the constant volumetric rate through each of the sensor and reference conduit tubes is monitored. The pressure difference between the monitored pressure in the sensor conduit tube and the pressure in the free space in the fuel tank above the surface of the remaining fuel is directly proportional to the weight of the fuel lying above the sensor conduit tube distal end. The density of the fuel is proportional to the monitored pressure difference between the sensor and reference conduit tubes, divided by the vertical spacing h. The calculated weight of the fuel, divided by the calculated density of the fuel, is proportional to the volume of the fuel remaining in the tank. *IRS data can be used to adjust the monitored differential pressure parameters for aircraft acceleration and attitude in the dynamic calculation of remaining fuel weight density and volume.*

32 Claims, 2 Drawing Sheets

FOREIGN PATENT DOCUMENTS

| | | |
|---|---|---|
| JP | 1982 44427 | 3/1982 |
| JP | 1990 231531 | 9/1990 |
| JP | 10 091246 A | 4/1998 |
| WO | WO02/29367 | 4/2002 |

* cited by examiner

PRESSURE-BASED AIRCRAFT FUEL CAPACITY MONITORING SYSTEM AND METHOD

Matter enclosed in heavy brackets [ ] appears in the original patent but forms no part of this reissue specification; matter printed in italics indicates the additions made by reissue.

RELATED APPLICATIONS

This application claims the benefit of U.S. Provisional Patent Application Ser. No. 60/679,752 which was filed on May 11, 2005*, and is a Reissue of U.S. Pat. No. 7,669,473, filed May 11, 2006, and issued Mar. 2, 2010.*

FIELD OF INVENTION

The present invention is broadly directed to the dynamic monitoring and measurement of the amount of fuel carried in a fuel tank of an aircraft and, more particularly, to systems and methods for dynamically determining the current weight, density and volume of fuel present in an aircraft fuel tank.

BACKGROUND OF THE INVENTION

Current aircraft fuel monitoring and indicating systems measure the fuel height and, separately, its density to calculate the weight of the fuel and, therefore, the remaining fuel capacity present in a fuel tank. In some such systems, for example, seven wired sensors, e.g. capacitive sensors, are variously placed about the bottom surface of the fuel tank—i.e. so that they are covered by the fuel in the tank. A predetermined profile is used to account for irregularities in the tank configuration/shape. These systems require that electrical current-carrying wires connected to the capacitive sensors be located within each fuel tank, with the consequent possibility of a spark that can ignite the fuel vapors and contained fuel and cause an in-flight explosion or fire, as is believed to have occurred in the crash of TWA Flight 800. Periodic inspection or prophylactic, periodically-scheduled replacement of such wiring located within the fuel tanks is both expensive and largely impractical for complex aircraft which are in virtually constant operation, requiring that the fuel tanks be fully drained of costly remaining fuel and the aircraft removed from service for an extended interval.

In recognition of the catastrophic effects of electrical sparking within an aircraft fuel tank containing fumes emitted by the fuel, and recognizing the impracticality of requiring regular inspection or replacement of such in-tank wiring, the U.S. Federal Aviation Administration (FAA) has recently mandated that commercial airlines pump nitrogen into aircraft fuel tanks to fill those volumetric portions of the tanks not containing fuel and thereby minimize the risk of such explosions and/or fire. This modification, however, provides but a limited remedy that, at most, reduces only the severity of the problem since the most likely existing sources of electrical sparks—i.e. electrical wiring associated with in-tank fuel sensors—nevertheless remain present within the fuel tanks of commercial aircraft.

OBJECTS AND SUMMARY OF THE INVENTION

It is accordingly the desideratum of the invention to provide a system and method for dynamically monitoring the amount of fuel remaining in an aircraft fuel tank without requiring in-tank electrical wiring that can initiate accidental ignition of fuel vapors in the tank.

It is a further object of the invention to provide such a system and method that provides the flight crew with continuously-updated indications of remaining fuel weight, density and volume in the fuel tank.

It is another object of the invention to provide such a system and method that can also be utilized in non-aircraft applications for dynamic monitoring of the amount of a liquid contained in a tank or vessel.

In one embodiment of the invention, a system for dynamically monitoring an amount of a liquid contained in a tank having a tank bottom includes a sensor conduit comprising a first fluid-delivery tube extending from a proximal end exterior of the tank to a distal open end located within the tank proximate the tank bottom; a reference conduit comprising a second fluid-delivery tube extending from a proximal end exterior of the tank to a distal open end located within the tank at a predetermined height above the tank bottom which defines a vertical spacing h between the first fluid-delivery tube open end and the second fluid-delivery tube open end; a regulating valve in each of the first and second fluid-delivery tubes exterior of the tank for delivering a substantially constant volume flow of a fluid to the distal open end of each of the first and second fluid-delivery tubes; a pressure sensor in each of the first and second fluid-delivery tubes between the regulating valve and the tank for dynamically measuring a current pressure in each of the sensor conduit and the reference conduit; and a controller for receiving the current pressure measurements from the pressure sensors in the first and second fluid-delivery tubes and which is operable for calculating at least one of the current weight of the liquid contained in the tank as a function of the measured current pressure in the sensor conduit, the density of the liquid contained in the tank as a function of a fraction in which the numerator is a pressure difference between the measured pressures in the first and second fluid-delivery tubes and the denominator is the vertical spacing h, and the current volume of the contained liquid as a function of a fraction in which the numerator is the calculated current weight of the contained liquid and the denominator is the calculated density of the contained liquid.

In another embodiment of the invention, a method for dynamically monitoring an amount of liquid contained in a tank having a tank bottom includes the steps of delivering a fluid into the contained liquid at a constant volumetric rate through a distal open end of a first fluid-delivery tube that extends from a proximal end exterior of the tank to the distal open end which is located within the tank proximate the tank bottom; measuring a first pressure of the fluid being delivered by the first fluid-delivery tube; calculating a weight of the contained liquid in the tank as a function of the measured first pressure; delivering the fluid into the contained liquid at a constant volumetric rate through a distal open end of a second fluid-delivery tube that extends from a proximal end exterior of the tank to the distal open end which is located within the tank at a predetermined height above the tank bottom that defines a vertical spacing h between the first fluid-delivery tube open end and the second fluid delivery tube open end; measuring a pressure difference between the fluid being delivered by the first fluid-delivery tube and the fluid being delivered by the second fluid-delivery tube; calculating a density of the contained liquid in the tank as a function of a fraction in which the numerator is the measured pressure difference and the denominator is the vertical spacing h; and calculating a volume of the contained liquid in the tank as a function of a fraction in which the numerator is the calculated weight of the contained liquid and the denominator is the calculated density of the contained liquid.

In still another embodiment of the invention, a system for dynamically monitoring a current weight, density and volume of liquid fuel contained in an aircraft fuel tank having a tank bottom, wherein the contained fuel fills the tank to a level that bounds a free space in the tank above the fuel level, includes a sensor conduit comprising a first fluid-delivery tube extending from a proximal end exterior of the tank to a distal open end located within the tank closely proximate the tank bottom; a reference conduit comprising a second fluid-delivery tube extending from a proximal end exterior of the tank to a distal open end located within the tank proximate the distal open end of said first fluid-delivery tube and at a predetermined vertical spacing h above the distal open end of said first fluid delivery tube; a regulating valve in each of the first and second fluid-delivery tubes exterior of the tank for delivering a substantially constant volumetric flow of nitrogen gas through the respective first and second fluid-delivery tube and outwardly from the distal open end of the respective first and second fluid-delivery tube into the fuel contained in the tank; a first differential pressure sensor for measuring a pressure difference between the nitrogen gas being delivered by the respective regulating valve through said first fluid-delivery tube and the free space in the fuel tank above the fuel level; a second differential pressure sensor for measuring a pressure difference between the nitrogen gas being delivered by the respective regulating valve through said first fluid-delivery tube and through said second fluid-delivery tube; and a controller connected to said first and second differential pressure sensors and operable for calculating the current weight of the fuel contained in the tank as a function of pressure difference measured by said first differential pressure sensor, for calculating the current density of the fuel contained in the tank as a function of a fraction in which the numerator is the pressure difference measured by said second differential pressure sensor and the denominator is the vertical spacing h, and for calculating the current volume of the fuel contained in the tank as a function of a fraction in which the numerator is the calculated current weight of the fuel contained in the tank and the denominator is the calculated current density of the fuel contained in the tank.

In yet another embodiment of the invention, a method for dynamically monitoring a current weight, density and volume of liquid fuel contained in an aircraft fuel tank having a tank bottom and in which the liquid fuel fills the tank to a level that bounds a free space in the tank above the fuel level includes the steps of delivering nitrogen gas into the liquid fuel in the tank at a constant volumetric rate through a distal open end of a first fluid-delivery tube that extends from a proximal end exterior of the tank to the distal open end which is located within the tank proximate the tank bottom; measuring a first pressure difference between the nitrogen gas being delivered by the first fluid-delivery tube and the free space in the tank; calculating the current weight of the liquid fuel in the tank as a function of the measured first pressure difference; delivering the nitrogen gas into the liquid fuel in the tank at the constant volumetric rate through a distal open end of a second fluid-delivery tube that extends from a proximal end exterior of the tank to the distal open end which is located within the tank at a predetermined height above the tank bottom that defines a vertical spacing h between the first fluid-delivery tube open end and the second fluid delivery tube open end; measuring a second pressure difference between the nitrogen gas being delivered by the first fluid-delivery tube and the nitrogen gas being delivered by the second fluid-delivery tube; calculating the current density of the liquid fuel in the tank as a function of a fraction in which the numerator is the measured second pressure difference and the denominator is the vertical spacing h; and calculating the current volume of the liquid fuel in the tank as a function of a fraction in which the numerator is the calculated current weight of the liquid fuel and the denominator is the calculated current density of the liquid fuel.

Other objects and features of the invention will become apparent from the following detailed description considered in conjunction with the accompanying drawings. It is to be understood, however, that the drawings are not drawn to scale and have been designed solely for purposes of illustration and not as a definition of the limits of the invention, for which reference should be made to the appended claims.

BRIEF DESCRIPTION OF THE DRAWINGS

In the drawings, wherein like reference numerals denote corresponding elements throughout the several Figures.

DETAILED DESCRIPTION OF THE PRESENTLY PREFERRED EMBODIMENTS

Figure 1:
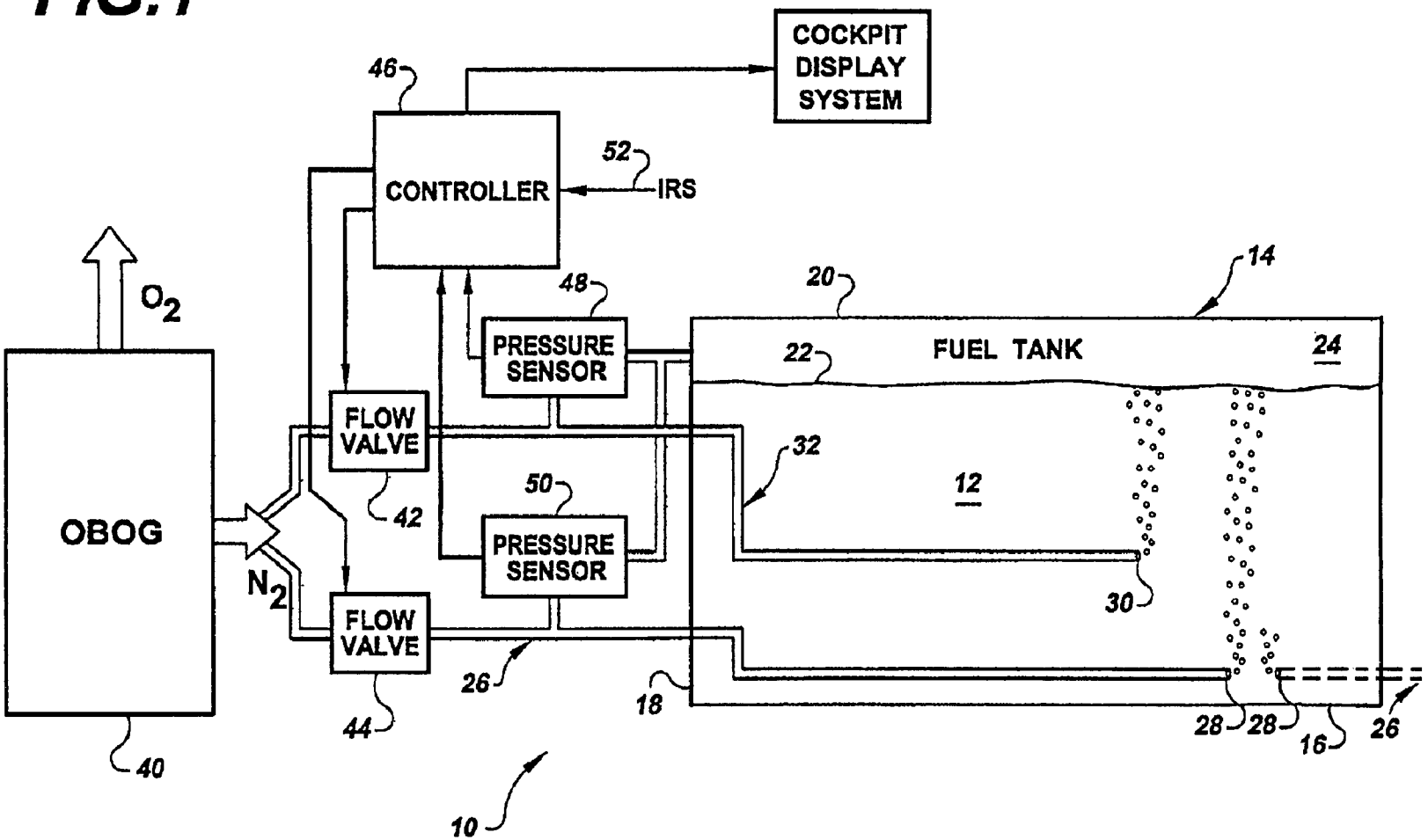
FIG. 1 is a schematic block diagram of a system constructed in accordance with the present invention for dynamically monitoring the current weight, density and volume of fuel contained in a fuel tank of an aircraft.

The present invention utilizes non-electric pressure transducers to dynamically provide a directly-measurable indication of the amount of fuel remaining in an aircraft fuel tank. In its most basic form, Teflon tubing is used to form fluid-conveying conduits that replace the prior art wired sensors. Thus, in one currently-preferred embodiment, at for example each tank bottom location of a prior art capacitive sensor, a distal open end of a length of Teflon tube is located closely proximate the tank bottom. The tubing is connected (exterior to the fuel tank) to a generator or supply of nitrogen, as for example an OBOG (On-Board Oxygen Generator) which has a semi-permeable membrane that, when pressure is applied to one side of the membrane, generates oxygen (which can be returned to the aircraft cabin) and nitrogen (for use in the inventive system). A relatively small, preferably constant volume flow of the OBOG-generated nitrogen is fed through each Teflon tube to bubble out through the distal tube outlet and up into the fuel contained in the fuel tank, thereby clearing the tube of liquid fuel. Exterior to the tank, a pressure sensor or transducer is connected to each tube to measure the pressure required to force the monitored flow of nitrogen into the tube and outwardly from the tube outlet into the liquid fuel in the tank. The pressure transducer also monitors the pressure of the nitrogen atmosphere that is maintained within the fuel tank above the contained volume of fuel—i.e. in that part of the fuel tank that is not filled with fuel.

Once the system has been calibrated, the measured difference in pressure between the nitrogen-emitting conduit whose distal outlet is located proximate the tank bottom and in the free or nitrogen-containing tank space above the fuel reservoir provides a direct measure of the weight of the column of fuel immediately above the conduit opening. This dynamic measure of the fuel weight is determined without any electrical wiring or connections—i.e. potential sources of electrical sparks—within the fuel tank. Use of the thus-measured fuel weights from the preferred plurality of such nitrogen-emitting conduits disposed variously throughout the fuel tank interior proximate its bottom surface dynamically provides a direct measurement of the weight of the fuel currently remaining in the tank.

In addition to the plural nitrogen-emitting conduit open ends disposed closely proximate the bottom of the fuel tank, in accordance with the invention a single additional "reference" conduit is disposed in the fuel tank with its distal open end located at a predetermined height above one of the tank bottom-located nitrogen-emitting conduit open ends. A preferably constant volume flow of OBOG-generated nitrogen is similarly fed to this reference conduit, which is likewise connected to a pressure sensor or transducer for measuring the pressure required to force the monitored flow of nitrogen into the reference conduit and outwardly from the distal reference conduit outlet into the liquid fuel in the tank. Thus, the open ends of the reference conduit and of one of the tank bottom-located conduits are disposed at a fixed, predetermined vertical spacing or separation or distance, with the reference conduit being located above, although not necessarily directly above, the tank bottom-located nitrogen-emitting conduit. The differential pressure measured between the reference conduit and the associated bottom-located conduit, divided by the predetermined spacing or distance between the two conduits, yields the density of the fuel contained in the tank. Once again, this determination of the density of the fuel is obtained without the need for electrical wiring or current paths or any other potential sources of electrical sparking within the fuel tank.

The volume of fuel contained in the fuel tank can additionally be calculated using the measured weight of the fuel in the tank and the determined fuel density. Knowledge of the actual volume of fuel remaining in the tank is essential to permit an aircraft fuel tank to be accurately "topped off" or otherwise filled with a known volume of fuel.

A pressure-based fuel capacity sensing system 10 constructed in accordance with a currently preferred embodiment of the invention is depicted in FIG. 1. The system 10 dynamically monitors the fuel 12 which is contained within a fuel tank 14, such as a fuel tank of an aircraft. Those skilled in the art will nevertheless recognize that the system and method of the invention, as herein described and claimed, can also be utilized and applied in non-aircraft environments and applications and, indeed, to monitor the weight, density and/or volume of liquids other than fuel, and there is no intention to limit the utility of the inventive system or method to aircraft or other vehicle-related applications. In any event, the fuel tank 14 of FIG. 1—which for ease of description is depicted as of generally rectangular shape—has a bottom 16, sidewalls 18 and a top 20 which bound its substantially closed (but typically vented) interior.

In FIG. 1, the fuel 12 in tank 14 does not entirely fill the tank. Thus, above the level or surface 22 of the contained volume of fuel 12 there is free or unfilled space 24. In commercial aircraft, the FAA currently requires that the space 24 in fuel tanks not containing fuel be filled with nitrogen gas to reduce the risk of explosion or fire potentially caused by a spark that can ignite fuel vapors present in the tank. Thus, although this description presupposes the presence of nitrogen gas in the space 24, the space 24 may alternatively be filled with any fluid as a function of the particular application and as a general matter of design choice without affecting the contemplated functionality and operability of the inventive system and method.

With continued reference to FIG. 1, at least one sensor conduit 26—and, at least in an aircraft fuel tank, more likely a plurality of such sensor conduits terminating at various locations about a typically irregularly-shaped fuel tank—is provided that enters the interior of the tank 14 and terminates at a distal open end 28 within the tank interior proximate, and preferably closely proximate, the tank bottom 16. The positioning of the open end 28 of sensor conduit 26 closely proximate the tank bottom 16 facilitates, as will hereinafter become apparent, accurate monitoring of the remaining fuel 12 present in tank 14 even when the tank contains only a relatively small volume of fuel. By way of illustration, the open end 28 of a sensor conduit 26 may for example be disposed in the range of approximately 2 to 6 cm above the tank bottom 16.

Also positioned within the interior of tank 14 is the distal open end 30 of a reference conduit 32 which, like the sensor conduit(s) 26, extends from its proximal end into the fuel tank through a suitable opening in, typically, either a sidewall 18 or the top 20 of the tank 14. Irrespective of the number of sensor conduits 26 whose distal open ends 28 are variously located in tank 14, only a single reference conduit 32 is required to provide the intended functionality associated with the reference conduit. The open end 30 of reference conduit 32 is located at a fixed position within tank 14, more particularly at a location proximate the open end 28 of sensor conduit 26 (or, where a plurality of sensor conduits 26 are disposed in tank 14, of a selected one of the sensor conduits 26) and at a predetermined height h above the open end 28 of sensor conduit 26. Put another way, the open end 30 of reference conduit 32 is spaced above the tank bottom 16 and proximate the open end 28 of sensor conduit 26 by a distance or separation that defines a predetermined vertical spacing h between the open ends 30, 28 of the respective conduits 32, 26. The spacing h may be selected as a general matter of design choice and in accordance with the particular application. The exact manner in which the conduit ends 26, 32 are maintained or fixed at their respective locations within tank 14 is also primarily a matter of design choice.

In currently preferred forms of the inventive system, the sensor and reference conduits 26, 32 are comprised of elongated lengths of tubes formed of or coated with Teflon or another polymer or the like having similar physical characteristics, although it is within the intended scope and contemplation of the invention that any sufficiently durable material capable of withstanding without degradation or damage the fuel (or other applicable liquid or fluid) in which the tubes are immersed within the tank and the nitrogen (or other gas or fluid) that the conduits are intended to operatively convey may alternatively be employed. The tubing that forms the conduits 26, 32 is of course hollow and its outer diameter(s), and the internal diameter(s) that defines the fluid passageway(s) through the tube(s), may be selected in accordance with the particular application as a general matter of design choice. In addition, the locations at which the sensor and reference conduits 26, 32 enter the tank 14 and are routed, within the tank, to the intended locations of their respective distal open ends 28, 30 may be determined to suit or as dictated by the particular application or otherwise selected as a matter of convenience, regulation, good engineering, design choice and/or any other factors deemed relevant thereto.

Figure 2:
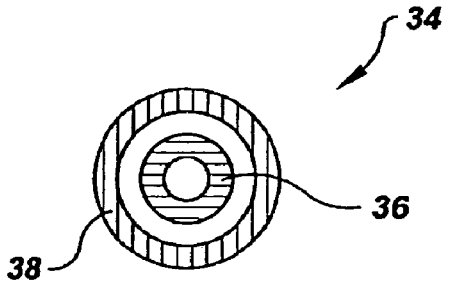
FIG. 2 is a cross-sectional view of an alternate form of the nitrogen gas delivery conduits in accordance with the invention.

In its most basic form, each of the sensor and reference conduits 26, 32 may be implemented as an appropriate length of hollow tubing defined by an outer wall of a suitable thickness bounding an internal passageway through which, by way of preferred example in the application herein described, nitrogen gas is fed from a location exterior of tank 14 to the respective conduit's distal open end 28, 30 positioned within the tank interior. A variety of alternate implementations of the conduits 26, 32 are additionally contemplated, such as that shown in the cross-sectional depiction of FIG. 2 in which one or each of the sensor and reference conduits 26, 32 may comprise a pair or set 34 of tubes disposed concentrically one within the other, so that the nitrogen or other fluid conveyed by the respective sensor or reference conduit is carried in the inner tube 36 and the concentrically-outer tube 38 defines a protective sheath for the inner tube. This arrangement additionally permits the inner tube 36—through which nitrogen gas is carried into the fuel tank 14 in the aircraft sensing system 10 herein described—to be readily removed and replaced by simply withdrawing the existing inner tube 36 from a location exterior of tank 14 (while the outer tube or sheath 38 remains in place) and rethreading or advancing a new inner tube 36 from such an exterior location along the length of outer tube 38 without having to first drain the tank of remaining fuel or otherwise open or enter or directly access the tank to perform such replacement of the nitrogen-delivery conduit. This additional, exceptionally advantageous functionality is particulary facilitated by, as is preferred, forming at least one of the inner and outer tubes 36, 38—and most preferably both—of Teflon or the like or with a Teflon or Teflon-like coating, although forming one or both of the tubes 36, 38 of other materials, as is contemplated in accordance with the invention, will also similarly permit ready remotely-effected replacement of inner tube 36 without requiring direct access to the tank interior. The difference in size between the outer diameter of the inner tube 36 and the inner wall diameter (i.e. the diameter of the interior passage) of the outer tube 38 may be selected as a matter of design choice to facilitate the aforedescribed remote replacement of the inner tube and/or to enhance the protective attributes of the outer tube which is disposed concentrically about the inner tube; it will be noted that the diametric spacing between the inner and outer tubes 36, 38 has been exaggerated in FIG. 2 for ease of explanation. As will be further apparent, it is also not required that the outer tube 38 disposed concentrically about inner tube 36 extend along the entire length of inner tube 36, so long as outer tube 38 forms a protective sheath about at least that length of inner tube 36 that extends within tank 14 and an additional length disposed sufficiently exterior of tank 14 to permit ready replacement, as described above, of inner tube 36 from a location exterior of the tank.

In currently preferred forms of the inventive system 10, each sensor and reference conduit 26, 32—or, where either is implemented by a concentric tube set 34, the inner tube 36 thereof—is connected at its proximal end exterior of fuel tank 14 to a source of nitrogen gas. Although any source of stored or locally generated nitrogen may be employed, in preferred forms of the invention the nitrogen is generated by the On-Board Oxygen Generators (OBOGs) which are already present on commercial aircraft for supplying the cockpit and passenger cabin with oxygen and which, as a byproduct of their operation, generate relatively small amounts of nitrogen gas.

Although the use of nitrogen gas in the herein-described and illustrated aircraft-based system 10 is preferred—both because the OBOGs provide a readily accessed, existing on-board source of nitrogen and because the free space 24 in an aircraft fuel tank 14 already contains nitrogen supplied to suppress accidental ignition of fuel vapors in the tank—any suitable gas, preferably an inert gas, can be employed in place thereof. Thus, the specification of nitrogen gas as the fluid delivered to and outwardly from the distal open ends of the sensor and reference conduits into the fuel contained in the aircraft fuel tank, as herein described, should be understood as being merely by way of preferred example and the use of other gases, such as inert gases, in its stead should be understood as within the intended scope and contemplation of the invention.

In any event, as by way of example shown in FIG. 1, the sensor and reference conduits 26, 32 are connected at their proximal ends to one or more OBOGs 40 or other source(s) of nitrogen gas. The flow of nitrogen carried by each of the sensor and reference conduits 26, 32 to its respective distal open end is regulated by a respective controlled flow valve 42, 44 that is inserted into the conduit exterior of tank 14. The volumetric flow of nitrogen through each of the sensor and reference conduits 26, 32 is regulated by a controller 46 which is operatively connected to each of the valves 42, 44. Controller 46 and its functionality as herein described may, by way of illustrative example, be implemented by a dedicated computer or circuitry of any suitable construction, or as a part of an existing computer or other hardware, software and/or circuitry already present in the aircraft for performing other functions, as a general matter of design choice.

The valves 42, 44 are operated to provide through each conduit 26, 32 a relatively small flow of nitrogen sufficient to cause the nitrogen to clear the conduit of fuel and bubble outwardly from the respective conduit open end 28, 30 into the fuel in tank 14. In preferred forms of the inventive system, controller 46 operates valves 42, 44 so that each conduit supplies nitrogen to its distal open end at a predetermined constant volumetric rate sufficient to assure continuous delivery of a relatively small volume of nitrogen into the contained fuel 12 under the most extreme anticipated conditions of fuel density, fuel quantity and acceleration forces and the like acting on the fuel in tank 14. In the most preferred embodiments of the invention, the valves 42, 44 are operated so that each of the sensor and reference conduits 26, 32 delivers nitrogen gas to its respective distal end at substantially the same volumetric flow rate.

Each of the sensor and reference conduits 26, 32 is also connected, exterior of tank 14 and downstream of nitrogen source 40 and its controlled flow valve 42, 44, to a respective differential pressure transducer or sensor 48, 50 which is, in turn, connected to controller 46. The pressure transducer 48 of sensor conduit 26 monitors the pressure difference between sensor conduit 26 and the tank free space 24 above the surface 22 of fuel 12, and communicates the monitored pressure difference to controller 46. The pressure transducer 50 of reference conduit 32 monitors the pressure difference between reference conduit 32 and the associated sensor conduit 26 located at a vertical spacing h from reference conduit 32, and likewise communicates that monitored pressure difference to controller 46. It will of course be appreciated that, alternatively, the pressure of each of the sensor and reference conduits 26, 32 and of the tank free space 24 can be individually monitored and communicated to controller 46 for calculation, by controller 46, of the differential pressures which in the preferred system of FIG. 1 are determined by the differential transducers 48, 50.

Once the system has been calibrated, the differential pressure monitored or calculated by using the output of pressure sensor 48 provides a dynamic—i.e. continuously updated—direct measure of the weight of the column of fuel immediately above the conduit opening. The controller 46, using the monitored differential pressures from all of the sensor conduits 26 in a fuel tank 14, can thus calculate—based on the known locations of the open ends 28 of the plural sensor conduits 26 in and the configuration of the tank 14—and output to a cockpit display screen or the like, for viewing by the aircraft flight crew, a continuously updated indication of the weight of the fuel 12 that remains in that tank. The cockpit display system forms no part of the present invention.

Since the spacing or height h between the open ends of the reference conduit 32 and an associated sensor conduit 26 is known, controller 46 can additionally calculate, based on the monitored difference in pressure between the sensor and reference conduits 26, 32, the density of the fuel 12 contained within tank 14, since the fuel density is proportional to the monitored pressure difference divided by the height h. The results of this calculation, too, can be output to a cockpit display system screen for viewing of the fuel density by the aircraft flight crew.

Finally, the volume of fuel remaining in tank 14—which is proportional to the fuel weight divided by its density—can be calculated in controller 46 to provide a continuously updated determination of the number of gallons of fuel present in the tank and thereby facilitate in-flight fuel conservation and management and, on the ground, more precise refueling operations. Here, as well, the calculated dynamic volume of fuel 12 that currently remains in tank 14 can be output from controller 46 to a cockpit display system screen for real-time viewing by the aircraft flight crew and the like.

In the embodiment of system 10 depicted in FIG. 1, controller 46 also receives as an input 52 relevant data from an inertial reference system (IRS) that is commonly present on commercial aircraft. The IRS data provides to controller 46 information relating to, inter alia, aircraft acceleration and attitude which, as should be apparent, can exert on the fuel 12 contained in an aircraft tank 14 forces that cause the fuel to variously shift or move about within the tank. The IRS data can thus be utilized by controller 46 to compensate or correct the differential pressure parameters monitored by the controller and thereby account for aircraft acceleration and attitude in the dynamic calculation of remaining fuel weight, density and volume.

As thus far discussed, the distal end of each sensor and reference conduit 26, 32 has been described as a respective open end 28, 30 through which nitrogen gas (or other fluid) is discharged into the fuel 12 contained in reservoir 14. It is currently intended and contemplated that each such conduit 26, 32, along at least the distal-most section of the tubing defined from its open end to a point closely proximate its open end, be disposed in a substantially horizontal orientation—i.e. so that the nitrogen gas emitted from the conduit's open end exits from a substantially horizontally-oriented section of tubing with the aircraft (or other structure within which the tank is disposed) in a substantially horizontal orientation. While this substantially horizontal orientation of the distal open ends 28, 30 of the respective sensor and/or reference conduits 26, 32 is currently preferred, it may nevertheless be varied to suit a particular application or otherwise as a matter of design choice. For example, where the delivered fluid is nitrogen gas which is less dense than aircraft jet fuel, the open end of either or both of the respective sensor and reference conduits may instead by oriented vertically downward, or at an angle between the horizontal and vertically downward directions.

Those skilled in the art will further recognize that G-forces and other directional forces exerted on the aircraft by accelerations and attitude changes will inevitably cause fuel 12 contained in an aircraft tank 14—particularly as the amount of fuel in the tank decreases—to slosh or shift or otherwise move about within the tank and, in doing so, affect the operation of the system 10 in ways that lessen the accuracy of the pertinent fuel parameter measurements and calculations. For example, as the level 22 of fuel 12 remaining in a tank 14 is reduced, the likelihood correspondingly increases that external forces on the aircraft, and likewise on the fuel, may cause the fuel to slosh or shift or otherwise move about within the tank such that one or more of the sensor conduit open ends 28 and/or the reference conduit open end 30 are momentarily no longer immersed in the fuel. Such perturbations in or shifting of the fuel 12 in tank 14 that still contains an appreciable volume of fuel can likewise affect the resulting fuel parameter calculations by momentarily raising or lowering the sensed conduit pressure required to maintain the predetermined volumetric flow of nitrogen gas through the respective conduit as fuel is driven directly toward or away from the conduit open end.

Figure 3:
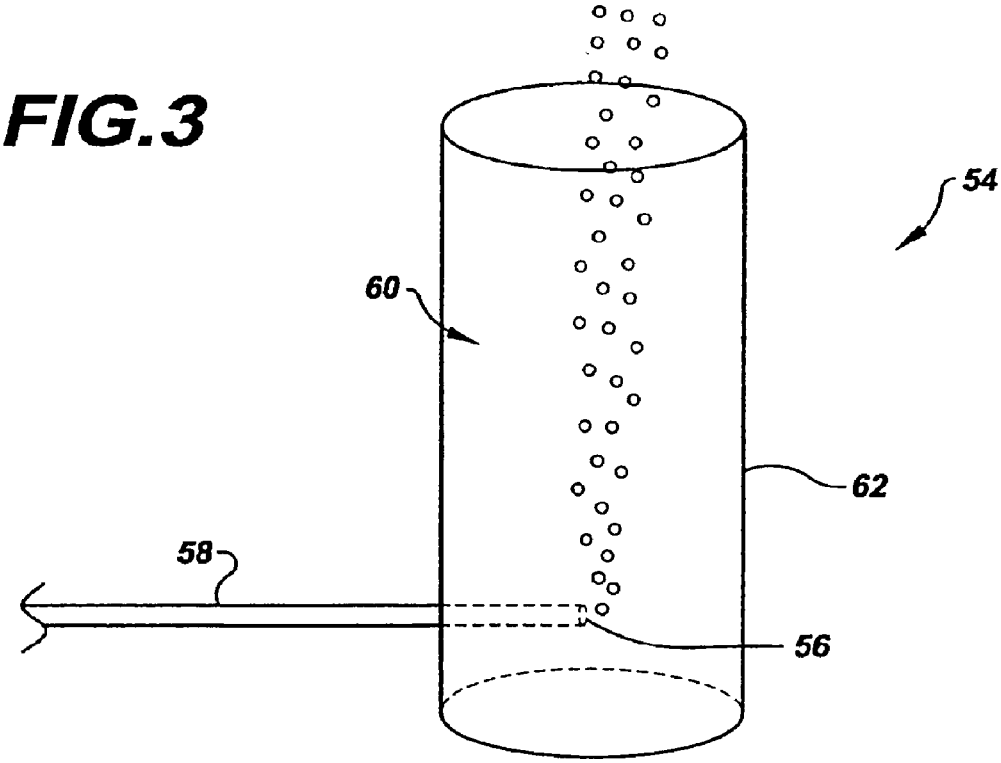
FIG. 3 is an elevated perspective view of a fluid perturbation damping structure in accordance with another aspect of the invention.

To reduce the effects on the system 10 of such inevitable shifting or movement of the fuel in a tank and thereby improve the reliability of the continuously-updated fuel parameter measurements and calculations, in most preferred forms of the invention the open ends 28, 30 of the respective sensor and reference conduits 26, 32 are surrounded by a partially enveloping structure 54, one such form of which is depicted by way of illustrative example in FIG. 3, for damping at least acceleration-initiated shifting or movement of the fuel. In the embodiment shown in FIG. 3, the open end 56 of a nitrogen delivery conduit 58—which may be any of the sensor and/or reference conduits 26, 32—is disposed so that the nitrogen gas carried by conduit 58 is delivered outwardly into the fuel 12 from its substantially horizontally-oriented open end. A substantially vertically-disposed cylinder 60 open at its top and bottom ends is mounted, in any suitable manner as a matter of design choice, so that the open end 56 of conduit 58 is disposed within the interior of cylinder 60 which thus forms a protective barrier for conduit open end 56 against momentary shifts in the fuel 12 contained in tank 14. The diameter and length of the cylinder 60 may be selected to suit a particular application or otherwise as a matter of design choice.

In the form of the damping structure depicted in FIG. 3, the conduit 58 enters the interior of cylinder 60 through an opening defined in its sidewall 62. Forms of the damping structure 54 in which, for example, the conduit enters the cylinder interior through one of its open ends, or otherwise as a matter of design choice, are also within the intended scope and contemplation of the invention, so long as the distal open end of the conduit 58 is located within the cylinder interior at the desired orientation and, of course, the effects on the system 10 of perturbations or movements of the fuel are adequately reduced.

Where the damping structure 54 is provided in respect of the distal end of a sensor conduit 26, it is as explained above most preferred that the conduit open end 56 be located relatively closely proximate the bottom 16 of the fuel tank 14. To facilitate its damping function, the sidewall 62 of cylinder 60 should protectively surround conduit open end 56 and, accordingly, it is generally intended that the open bottom end of cylinder 60 be located relatively close to—but preferably not in abutment with—the tank bottom 16, as for example about 2 to 3 cm above the tank bottom 16 where the open end 56 of conduit 58 is positioned approximately 3 to 6 cm above the tank bottom. This will inherently locate the conduit open end 56 relatively close to the lower end of damping cylinder 60, as for example depicted in FIG. 3.

Where on the other hand the damping structure 54 is provided in respect of the distal end of the reference conduit 32, the conduit open end 56 may be disposed within the cylinder sidewall 62 at any desired location along the length of cylinder 60. It is in any event anticipated that the relative positioning of the conduit open end 56 protectively within the cylinder sidewall 62 and along the length of cylinder 60 in implementing the distal end of reference conduit 32 will be selected to minimize the effects of shifting fuel but, of course, may also be determined on the basis of other factors relevant to the particular application and/or any other aspects related to a specific implementation of the inventive system 10. Thus, the conduit open end 56 can in any event be positioned, as appropriate for any of the sensor and/or reference conduits, within the cylinder sidewall 62 at any desired or suitable location along the length of damping cylinder 60 between its open top and bottom ends.

Although it is generally contemplated that the cylinder sidewall 62 be continuous and solid and uninterrupted, embodiments of the damping structure 54 in which predeterminately-located openings or other discontinuities are defined in sidewall 62 that variously interrupt the solidity or continuity of sidewall 62—or that define a series of associated sidewalls or sidewall pieces—to enhance the dampening effect of the structure 54 are also within the intended scope of the invention.

It should also be appreciated that although the method and system 10 as herein depicted and described are primarily intended for use in monitoring the weight, density and/or volume of liquid fuel contained in a tank, such as a fuel tank of an aircraft or other vehicle, they may also be applied or implemented in applications in which it is desired to monitor the parameters or characteristics of any liquid contained in a tank or vessel or any other full or partial enclosure, such for example as manufacturing plant environments and environmentally extreme applications in which ready access to the liquid container may be limited or impractical. In monitoring the relevant parameters of a contained liquid other than fuel, it will be apparent that the gas—or, depending on the nature of the contained liquid, any other fluid that is conveyed into the contained liquid by the sensor and/or reference conduits should be selected so as to be, at the very least, inert or nonreactive and insoluble with the contained liquid, and the use of a gas (such as an inert gas) that is less dense than the contained liquid being monitored is generally preferred. In any event, all such alternative applications should be considered to be within the intended scope and contemplation of the invention.

Thus, while there have shown and described and pointed out fundamental novel features of the invention as applied to preferred embodiments thereof, it will be understood that various omissions and substitutions and changes in the form and details of the methods described and systems and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A system for dynamically monitoring an amount of a liquid contained in a tank having a tank bottom, the liquid contained in the tank has a level that bounds free space in the tank above the liquid lever, said system comprising:

at least one sensor conduit comprising a first fluid-delivery tube extending from a proximal end exterior of the tank to a distal open end located within the tank proximate the tank bottom;

a reference conduit comprising a second fluid-delivery tube extending from a proximal end exterior of the tank to a distal open end located within the tank at a predetermined height above the tank bottom which defines a vertical spacing h between the first fluid-delivery tube open end and the second fluid-delivery tube open end;

a regulating valve in each of the first and second fluid-delivery tubes exterior of the tank for delivering a substantially constant volume flow of a fluid to the distal open end of each of the first and second fluid-delivery tubes;

a pressure sensor in each of the first and second fluid-delivery tubes between the regulating valve and the tank for dynamically measuring a current pressure in each of the sensor conduit and the reference conduit, the pressure sensor in said first fluid-delivery conduit is connected to said free space; and a controller for receiving the current pressure measurements from the pressure sensors in the first and second fluid-delivery tubes and operable for continuously calculating at least one of the current weight of the liquid contained in the tank as a function of the measured current pressure in the sensor conduit, the density of the liquid contained in the tank as a function of a fraction in which the numerator is a pressure difference between the measured pressures in the first and second fluid-delivery tubes and the denominator is the vertical spacing h, and the current volume of the contained liquid as a function of a fraction in which the numerator is the calculated current weight of the contained liquid and the denominator is the calculated density of the contained liquid, wherein the pressure sensor in said first fluid-delivery tube continuously outputs to said controller a pressure difference between said first fluid-delivery conduit and said free space.

2. A system in accordance with claim 1, wherein said controller operatively calculates the current weight of the contained fuel as a function of the output pressure difference between said first fluid-delivery conduit and said free space.

3. A system in accordance with claim 1, wherein the pressure sensor in said first fluid-delivery conduit outputs to said controller a differential pressure between the first fluid-delivery conduit and said free space, wherein the pressure sensor in said second fluid-delivery conduit outputs to said controller a differential pressure between the first fluid-delivery conduit and the second fluid-delivery conduit, and wherein said controller operatively calculates the current weight of the contained fuel as a function of the output pressure difference between said first fluid-delivery conduit and said free space.

4. A system in accordance with claim 1, wherein the tank is a fuel tank, the liquid is fuel, and the fluid is nitrogen gas.

5. A system in accordance with claim 1, further comprising a plurality of said sensor conduits, each of said sensor conduits comprising a first fluid-delivery tube extending from a proximal end exterior of the tank to a distal open end located at a different location within the tank proximate the tank bottom; and wherein the current weight of the contained fuel is calculated by said controller as a function of the measured current pressures in the plural sensor conduits.

6. A system in accordance with claim 1, wherein at least one of said sensor conduit and said reference conduit further comprises a third length of tubing defining a protective sheath concentrically about the fluid-delivery tube and concentrically covering the fluid-delivery tube at least within the liquid containing tank, said third length of tubing being sized to permit sliding movement of the fluid-delivery tube within and along said third length of tubing to facilitate remote sliding withdrawal and replacement of the fluid-delivery tube concentrically within said third length of tubing without requiring direct access to the interior of the fuel tank in which the fuel is contained.

7. A system for dynamically monitoring an amount of a liquid contained in a tank having a tank bottom, said system comprising:

a sensor conduit comprising a first fluid-delivery tube extending from a proximal end exterior of the tank to a distal open end located within the tank proximate the tank bottom;

a reference conduit comprising a second fluid-delivery tube extending from a proximal end exterior of the tank to a distal open end located within the tank at a predetermined height above the tank bottom which defines a vertical spacing h between the first fluid-delivery tube open end and the second fluid-delivery tube open end;

a regulating valve in each of the first and second fluid-delivery tubes exterior of the tank for delivering a substantially constant volume flow of a fluid to the distal open end of each of the first and second fluid-delivery tubes;

a pressure sensor in each of the first and second fluid-delivery tubes between the regulating valve and the tank for dynamically measuring a current pressure in each of the sensor conduit and the reference conduit a controller for receiving the current pressure measurements from the pressure sensors in the first and second fluid-delivery tubes and operable for calculating at least one of the current weight of the liquid contained in the tank as a function of the measured current pressure in the sensor conduit, the density of the liquid contained in the tank as a function of a fraction in which the numerator is a pressure difference between the measured pressures in the first and second fluid-delivery tubes and the denominator is the vertical spacing h, and the current volume of the contained liquid as a function of a fraction in which the numerator is the calculated current weight of the contained liquid and the denominator is the calculated density of the contained liquid; and a damping structure disposed at the distal open end of at least one of said first and second fluid-delivery conduits, said damping structure comprising a sidewall protectively surrounding said distal open end to shield the distal open end from shifts of the contained liquid.

8. A system in accordance with claim 7, wherein said sidewall defines a cylinder disposed in a substantially vertical orientation and having open top and bottom ends of the cylinder.

9. A system in accordance with claim 1, wherein said distal open end of each of the first and second fluid-delivery conduits is oriented so that the fluid is delivered from said open ends in a substantially horizontal orientation.

10. A method for dynamically monitoring an amount of liquid contained in a tank having a tank bottom, the liquid contained in the tank has a level that bounds free space in the tank above the liquid level, comprising the steps of:

delivering a fluid into the contained liquid at a constant volumetric rate through a distal open end of a first fluid-delivery tube tat extends from a proximal end exterior of the tank to the distal open end which is located within the tank proximate the tank bottom;

continuously measuring a first pressure of the fluid being delivered by the first fluid-delivery tube said step of measuring a first pressure comprises measuring a pressure difference between the fluid being delivered by the first fluid-delivery tube and the free space in the tank;

calculating a weight of the contained liquid in the tank as a function of the measured first pressure;

delivering the fluid into the contained liquid at a constant volumetric rate through a distal open end of a second fluid-delivery tube that extends from a proximal end exterior of the tank to the distal open end which is located within the tank at a predetermined height above the tank bottom that defines a vertical spacing h between the first fluid-delivery tube open end and the second fluid delivery tube open end;

continuously measuring a pressure difference between the fluid being delivered by the first fluid-delivery tube and the fluid being delivered by the second fluid-delivery tube;

calculating a density of the contained liquid in the tank as a function of a fraction in which the numerator is the measured pressure difference and the denominator is the vertical spacing h; and calculating a volume of the contained liquid in the tank as a function of a fraction in which the numerator is the calculated weight of the contained liquid and the denominator is the calculated density of the contained liquid.

11. A method in accordance with claim 10, wherein the tank is a fuel tank, the liquid is fuel, and the fluid is nitrogen gas.

12. A method in accordance with claim 10, wherein the fluid is delivered through the first and second fluid-delivery tubes at substantially the same constant volumetric rate.

13. A method in accordance with claim 10, wherein the tank is a closed fuel tank of an aircraft, the liquid is aircraft fuel and the fluid is nitrogen gas.

14. A method in accordance wit claim 13, wherein the nitrogen gas for delivery by the first and second fluid-delivery tubes is supplied by an On-Board Oxygen Generator.

15. A method in accordance with claim 13, further comprising the step of supplying at least one of the calculated weight of the contained fluid, the calculated density of the contained fluid, and the calculated volume of the contained fluid for viewing by an aircraft flight crew on a cockpit display for real-time monitoring of the amount of fuel contained in the fuel tank.

16. A system for dynamically monitoring a current weight, density and volume of liquid fuel contained in an aircraft fuel tank having a tank bottom, the contained fuel filling the tank to a level that bounds a free space in the tank above the fuel level, said system comprising:

a sensor conduit comprising a first fluid-delivery tube extending from a proximal end exterior of the tank to a distal open end located within the tank closely proximate the tank bottom;

a reference conduit comprising a second fluid-delivery tube extending from a proximal end exterior of the tank to a distal open end located within the tank proximate the distal open end of said first fluid-delivery tube and at a predetermined vertical spacing h above the distal open end of said first fluid delivery tube;

a regulating valve in each of the first and second fluid-delivery tubes exterior of the tank for delivering a substantially constant volumetric flow of nitrogen gas though the respective first and second fluid-delivery tube and outwardly from the distal open end of the respective first and second fluid-delivery tube into the fuel contained in the tank;

a first differential pressure sensor for continuously measuring a pressure difference between the nitrogen gas being delivered by the respective regulating valve through said first fluid-delivery tube and the free space in the fuel tank above the fuel level;

a second differential pressure sensor for continuously measuring a pressure difference between the nitrogen gas being delivered by the respective regulating valve though said first fluid-delivery tube and through said second fluid-delivery tube; and a controller connected to said first and second differential pressure sensors and operable for calculating the current weight of the fuel contained in the tank as a function of pressure difference measured by said first differential pressure sensor, for calculating the current density of the fuel contained in the tank as a function of a fraction in which the numerator is the pressure difference measured by said second differential pressure sensor and the denominator is the vertical spacing h, and for calculating the current volume of the fuel contained in the tank as a function of a fraction in which the numerator is the calculated current weight of the fuel contained in the tank and the denominator is the calculated current density of the fuel contained in the tank.

17. A system in accordance with claim 16, further comprising an On-Board Oxygen Generator for supplying the nitrogen gas to said first and second fluid-delivery conduits for delivery into the fuel contained in the tank through the open distal ends of the first and second fluid-delivery conduits.

18. A system for dynamically monitoring a current weight, density and volume of liquid fuel contained in an aircraft fuel tank having a tank bottom, the contained fuel filling the tank to a level that bounds a free space in the tank above the fuel level, said system comprising:

a sensor conduit comprising a first fluid-delivery tube extending from a proximal end exterior of the tank to a distal open end located within the tank closely proximate the tank bottom;

a reference conduit comprising a second fluid-delivery tube extending from a proximal end exterior of the tank to a distal open end located within the tank proximate the distal open end of said first fluid-delivery tube and at a predetermined vertical spacing h above the distal open end of said first fluid delivery tube;

a regulating valve in each of the first and second fluid-delivery tubes exterior of the tank for delivering a substantially constant volumetric flow of nitrogen gas though the respective first and second fluid-delivery tube and outwardly from the distal open end of the respective first and second fluid-delivery tube into the fuel contained in the tank;

a first differential pressure sensor for measuring a pressure difference between the nitrogen gas being delivered by the respective regulating valve through said first fluid-delivery tube and the free space in the fuel tank above the fuel level;

a second differential pressure sensor for measuring a pressure difference between the nitrogen gas being delivered by the respective regulating valve through said first fluid-delivery tube and through said second fluid-delivery tube; and a controller connected to said first and second differential pressure sensors and operable for calculating the current weight of the fuel contained in the tank as a function of pressure difference measured by said first differential pressure sensor, for calculating the current density of the fuel contained in the tank as a function of a fraction in which the numerator is the pressure difference measured by said second differential pressure sensor and the denominator is the vertical spacing h, and for calculating the current volume of the fuel contained in the tank as a function of a fraction in which the numerator is the calculated current weight of the fuel contained in the tank and the denominator is the calculated current density of the fuel contained in the tank; and a fuel perturbation damping structure disposed at the distal open end of at least one of the first and second fluid-delivery tubes, said damping structure comprising a sidewall protectively surrounding at least a portion of said distal open end to shield the distal open end from shifts of the fuel contained in the tank.

19. A system in accordance with claim 18, wherein said sidewall defines a cylinder disposed in a substantially vertical orientation and having open top and bottom ends of the cylinder.

20. A system in accordance with claim 16, wherein at least one of the sensor conduit and the reference conduit further comprises a third length of tubing defining a protective sheath concentrically about the fluid-delivery tube and concentrically covering the fluid-delivery tube at least within the tank, said third length of tubing being sized to permit sliding movement of the fluid-delivery tube within and along said third length of tubing to facilitate remote sliding withdrawal and replacement of the fluid-delivery tube concentrically within said third length of tubing without requiring direct access to the interior of the fuel tank in which the fuel is contained.

21. A system in accordance with claim 20, wherein said third length of tubing and the fluid-delivery tube of said at least one of said sensor conduit and said reference conduit comprising Teflon.

22. A method for dynamically monitoring a current weight, density and volume of liquid fuel contained in an aircraft fuel tank having a tank bottom and in which the liquid fuel fills the tank to a level that bounds a free space in the tank above the libel level, comprising the steps of:

delivering nitrogen gas into the liquid fuel in the tank at a constant volumetric rate though a distal open end of a first fluid-delivery tube that extends from a proximal end exterior of the tank to the distal open end which is located within the tank proximate the tank bottom;

continuously measuring a first pressure difference between the nitrogen gas being delivered by the first fluid-delivery tube and the free space in the tank;

calculating the current weight of the liquid fuel in the tank as a function of the measured first pressure difference;

delivering the nitrogen gas into the liquid fuel in the tank at the constant volumetric rate trough a distal open end of a second fluid-delivery tube tat extends from a proximal end exterior of the tank to the distal open end which is located within the tank at a predetermined height above the tank bottom that defines a vertical spacing h between the first fluid-delivery tube open end and the second fluid delivery tube open end;

continuously measuring a second pressure difference between the nitrogen gas being delivered by the first fluid-delivery tube and the nitrogen gas being delivered by the second fluid-delivery tube;

calculating the current density of the liquid fuel in the tank as a function of a fraction in which the numerator is the measured second pressure difference and the denominator is the vertical spacing h; and continuously calculating the current volume of the liquid fuel in the tank as a function of a fraction in which the numerator is the calculated current weight of the liquid fuel and the denominator is the calculated current density of the liquid fuel.

*23. A system for dynamically monitoring an amount of liquid contained in a fuel tank on an aircraft, said fuel tank having a tank bottom, the liquid contained in the fuel tank comprising fuel for the aircraft and having a level that bounds free space in the fuel tank above the liquid level, said system comprising at least one sensor conduit comprising a first fluid-delivery tube extending from a proximal end exterior of the fuel tank to a distal open end located within the fuel tank proximate the tank bottom; a reference conduit comprising a second fluid-delivery tube extending from a proximal end exterior of the fuel tank to a distal open end located within the fuel tank at a predetermined height above the tank bottom which defines a vertical spacing h between the first fluid-delivery tube open end and the second fluid-delivery tube open end; said first and second delivery tubes delivering a substantially constant volume flow of a fluid to the distal open end thereof; a pressure sensor in each of the first and second fluid-delivery tubes disposed for dynamically measuring a current pressure in each of the sensor conduit and the reference conduit, the pressure sensor in said first fluid-delivery conduit is connected to said free space; a controller for receiving the current pressure measurements from the pressure sensors in the first and second fluid-delivery tubes and operable for continuously calculating at least one of the current weight of the liquid contained in the tank as a function of the measured current pressure in the sensor conduit, the density of the liquid contained in the tank as a function of a fraction in which the numerator is a pressure difference between the measured pressures in the first and second fluid-delivery tubes and the denominator is the vertical spacing h, and the current volume of the contained liquid as a function of a fraction in which the numerator is the calculated current weight of the contained liquid and the denominator is the calculated density of the contained liquid, the pressure sensor in said first fluid-delivery tube continuously outputting to said controller a pressure difference between said first fluid-delivery conduit and said free space; and a source of data relating to acceleration and attitude of the aircraft operatively connected to an input to the controller, the controller receiving said data and dynamically adjusting said received pressure measurements in accordance therewith; whereby aircraft acceleration and attitude is accounted for in the dynamic calculation of remaining fuel weight, density and volume.*

*24. A system in accordance with claim 23 wherein said source of data is an inertial reference system on board said aircraft.*

*25. A system in accordance with claim 24 wherein the fluid is nitrogen gas.*

*26. A system in accordance with claim 23 wherein the fluid is nitrogen gas.*

*27. A system in accordance with claim 23 wherein said controller operatively calculates the current weight of the contained fuel as a function of the output pressure difference between said first fluid-delivery conduit and said free space dynamically adjusted in accordance with said received data relating to acceleration and attitude of the aircraft.*

*28. A method for dynamically monitoring an amount of liquid contained in a fuel tank on an aircraft, said fuel tank having a tank bottom, the liquid contained in the fuel tank comprising fuel for the aircraft and having a level that bounds free space in the fuel tank above the liquid level, the method comprising the steps of delivering a fluid into the contained liquid through a distal open end of a first fluid-delivery tube that extends from a proximal end exterior of the tank to the distal open end which is located within the tank proximate the tank bottom; continually measuring a first pressure of the fluid being delivered by the first fluid-delivery tube, said step of measuring a first pressure comprises measuring a pressure difference between the fluid being delivered by the first fluid-delivery tube and the free space in the tank; calculating a weight of the contained liquid in the tank as a function of the measured first pressure; delivering the fluid into the contained liquid at essentially a constant volumetric rate through a distal open end of a second fluid-delivery tube that extends from a proximal end exterior of the tank to the distal open end which is located in the tank at a predetermined height above the tank bottom that defines a vertical spacing h between the first fluid-delivery tube open end and the second fluid-delivery tube open end; continuously measuring a pressure between the fluid being delivered by the first fluid-delivery tube and the fluid being delivered by the second fluid-delivery tube: providing data relating to acceleration and attitude of the aircraft and dynamically adjusting the measured pressure differential in accordance with said acceleration and aircraft attitude; calculating an adjusted density of the contained liquid in the tank as a function of a fraction in which the numerator is the measured pressure difference and the denominator is the vertical spacing h; and calculating a volume of the contained liquid in the tank as a function of a fraction in which the numerator is the calculated weight of the contained liquid and the denominator is the calculated density of the contained liquid; whereby aircraft acceleration and attitude is accounted for in the dynamic calculation of remaining fuel weight, density and volume.*

*29. A method in accordance with claim 28 wherein said acceleration and attitude data providing step comprises providing said data from an inertial reference system on board the aircraft.*

*30. A method in accordance with claim 29 wherein the fluid is nitrogen gas.*

*31. A method in accordance with claim 28 wherein the fluid is nitrogen gas.*

*32. A method in accordance with claim 28 further comprising calculating the current weight of the contained fuel as a function of the output pressure differential between the first fluid-delivery conduit and the free space dynamically adjusted in accordance with the provided data relating to acceleration and attitude of the aircraft.*

* * * * *